United States Patent [19]

Funk et al.

[11] Patent Number: 4,651,719
[45] Date of Patent: Mar. 24, 1987

[54] CONTINUOUS PASSIVE MOTION SHOULDER UNIT

[75] Inventors: Daniel A. Funk, Rochester, Minn.; Jan B. Yates, Reynoldsburg, Ohio

[73] Assignee: Danninger Medical Technology, Inc., Columbus, Ohio

[21] Appl. No.: 693,671

[22] Filed: Jan. 22, 1985

[51] Int. Cl.$^4$ .............................................. A61F 5/01
[52] U.S. Cl. ..................................... 128/25 R; 128/77
[58] Field of Search ................... 128/24 R, 24.2, 25 R, 128/25 B, 82.1, 83, 84 C, 85, 77, 78, 87 C, 88; 3/1.1, 1.2, 12, 12.1

[56] References Cited

U.S. PATENT DOCUMENTS

| | | | |
|---|---|---|---|
| 2,777,439 | 1/1957 | Tuttle | 128/25 |
| 2,832,334 | 4/1958 | Whitelaw | 128/25 R |
| 3,089,700 | 5/1963 | Hotas | 272/117 |
| 3,929,335 | 12/1975 | Malick | 272/57 R |
| 3,976,057 | 8/1976 | Barclay | 128/25 R |
| 4,214,577 | 7/1980 | Hoy | 128/25 R |
| 4,395,039 | 7/1983 | Kaiser | 272/126 |
| 4,487,199 | 12/1984 | Saringer | 128/25 R |
| 4,577,623 | 3/1986 | Pecheux | 128/25 R |

FOREIGN PATENT DOCUMENTS

| | | | |
|---|---|---|---|
| 1280471 | 10/1968 | Fed. Rep. of Germany | 128/87 R |
| 2524468 | 12/1976 | Fed. Rep. of Germany | |
| 2440187 | 5/1980 | France | |
| 2535605 | 5/1984 | France | 128/25 R |
| 159947 | 3/1962 | U.S.S.R. | 128/25 R |

OTHER PUBLICATIONS

Kinetec Shoulder Exerciser, pp. 1-4, Richards Medical Company.

*Primary Examiner*—Richard J. Apley
*Assistant Examiner*—John L. Welsh
*Attorney, Agent, or Firm*—Pearne, Gordon, McCoy & Granger

[57] ABSTRACT

A lightweight portable device is provided to impart continuous passive motion to a user's shoulder. The device causes abduction and adduction and has the option of causing simultaneous rotation as well through use of a single actuator. The base of the device is curved to fit against a lateral portion of the user's torso and the device is held in position by a harness. An upper arm support is pivotally connected to and extends laterally from the base. A linear actuator extends between and is linked to the upper arm support and the base to cause abduction and adduction of the arm. A forearm support which is pivotally connected to the upper arm support and is also angularly adjustable relative to the upper arm support is linked to the base to cause rotation of the forearm support as the upper arm support is pivoted. The range of rotation can be varied or eliminated. The degree and speed of abduction and adduction can also be varied. The device is contained in a housing having a chamber with an extendable, two-part cover so that the operating mechansim is concealed.

19 Claims, 10 Drawing Figures

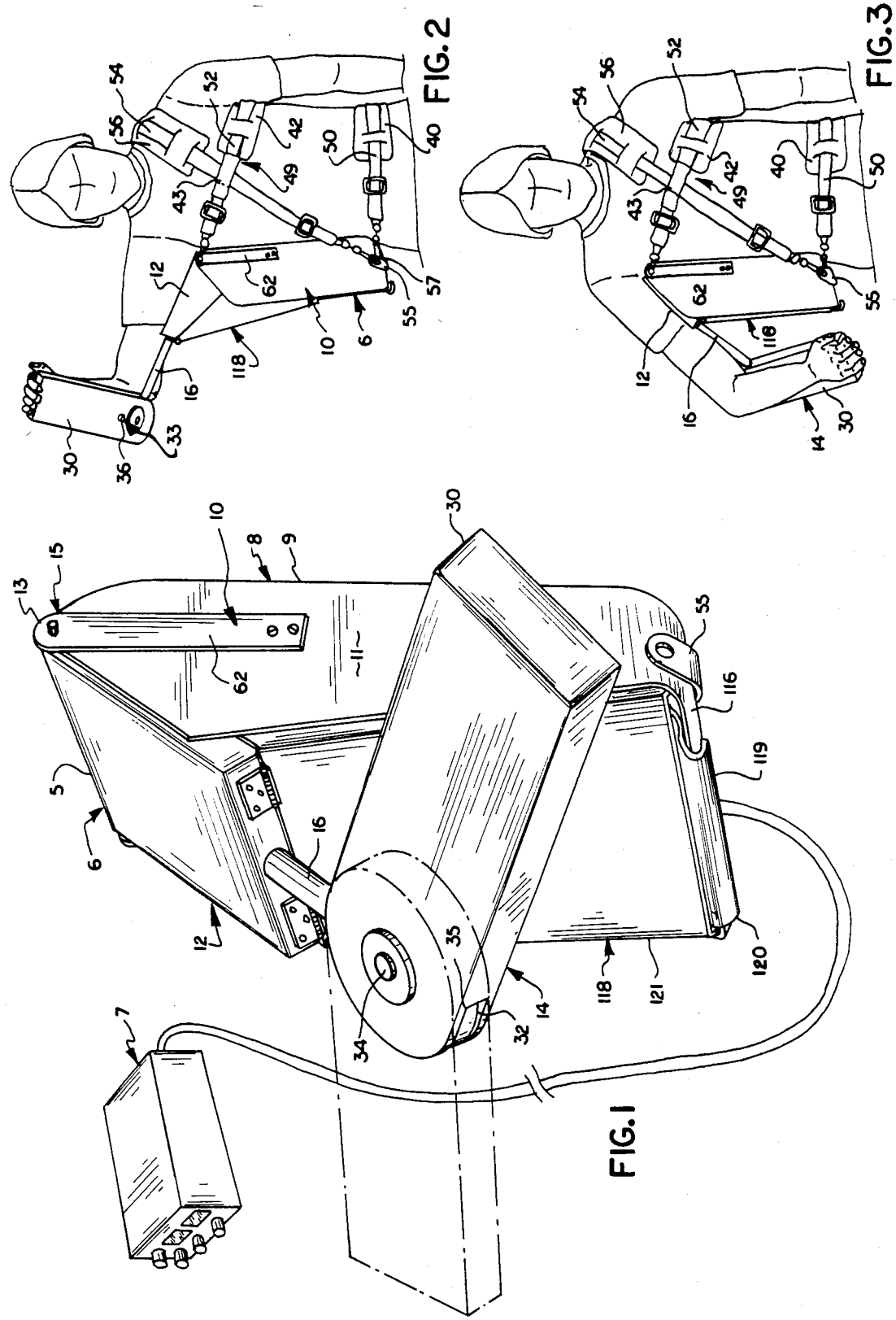

CONTINUOUS PASSIVE MOTION SHOULDER UNIT

BACKGROUND OF THE INVENTION

The invention relates to an apparatus which is used for therapeutic treatment of a shoulder joint. In particular, the device can be used to impart continuous passive motion ("CPM") to a shoulder. This device is portable, and the device can be worn by the patient to allow for patient mobility. The device can impart both abduction and rotation to the shoulder.

Continuous passive motion therapy is used to aid in recovery following joint trauma and has been found to have beneficial results in the rehabilitation of injured limbs. Passive motion is also used for treatment of other bone and muscular disorders, such as arthritis and muscular dystrophy. Often a physical therapist must apply the passive motion.

Many devices are currently commercially available for application of continuous passive motion to the hip, leg and foot. An example of such a device is shown in German Offenlegungsschrift No. 25 24 468 to Lang. This publication also shows a device to cause flexion of the wrist and elbow. Other devices which cause continuous passive flexion of the elbow and wrist are illustrated in French Pat. No. 2,440,187 to Pecheux, U.S. Pat. No. 3,929,335 to Malick, and U.S. Pat. No. 4,487,199 to Sarringer.

It is more difficult to design a device to impart the desired passive treatment to the shoulder than to the elbow or wrist, in part because of its proximity to the torso, and in part because of the greater range of mobility in the shoulder. Devices for exercising the shoulder joint are shown in U.S. Pat. No. 2,777,439 to Tuttle, U.S. Pat. No. 3,089,700 to Hotas, and U.S. Pat. No. 4,395,039 to Kaiser.

The shoulder is formed where the clavicle, scapula and humerus join laterally. The joint formed is a ball-and-socket type articulation between the proximal humerus and the glenoid cavity of the scapula. The socket is shallow, and the joint capsule is loose-fitting. As a result of this construction, the joint permits a wide range of motion but the joint is subject to poor stability and strength.

The shoulder is capable of three types of motion: abduction and adduction, flexion and extension, and rotation. Abduction and adduction is movement of the arm away from and toward the median axis, or long axis, in the median plane of the body. The median plane of the body is defined by the front or back of the body in a straight position. Abduction is movement away from the median axis, such as raising an arm laterally or sideways. Adduction is the opposite movement, i.e., movement toward the median axis of the body. Flexion means moving the arm forward and upward or backward and upward to increase the angle between the arm and the median plane of the body. Extension is the opposite motion of flexion, i.e., movement toward the median plane of the body. Rotation is turning the arm about its long axis as if on a pivot. External rotation is rotation away from the median axis of the body and internal rotation is rotation toward the median axis of the body.

Following shoulder surgery, it is desirable to recover abduction and adduction, and rotation in the shoulder joint. If abduction and adduction can be recovered, flexion and extension will also be possible.

The current invention presents a device for passively inducing abduction and adduction of the arm about the shoulder, and optionally causing simultaneous rotation of the arm as well. The device fits against the lateral portion of the torso under the shoulder to be exercised and provides support for the upper arm and the forearm. It exercises the shoulder by raising the upper arm and forearm supports, which pushes the arm upward to cause abduction and external rotation, and by supporting the arm against its own weight to cause controlled adduction and internal rotation. The device permits variable angles of abduction and rotation, as well as variable speeds of motion.

Another feature of continuous passive motion devices which is desirable is portability. These devices may be transported from room to room in order to enable different patients to share a CPM machine.

It is of even further advantage if the device is designed to allow the patient to wear the device since the patient may be subjected to continuous treatment. The patient may thus remain mobile while being subjected to CPM treatment.

It is a further advantage to present a CPM unit which can be easily adapted for use with the right shoulder as well as the left shoulder.

It is also of advantage to provide a CPM structure which can be adjusted according to the angle of flexion desired at the elbow, and to adapt to patients of varying size and shape.

Finally, in the interests of safety, it is an advantage for the CPM device to be designed so that a minimum of the actuator mechanism is exposed. If the operating parts of the device are concealed, it reduces the risk of a patient's being pinched by the machine, or bed clothes getting caught in the mechanism.

SUMMARY OF THE INVENTION

The device of the present invention includes a base which is positioned under the arm of the user adjacent to the lateral portion of the torso. An upper arm support is hinged to the base and extends away from the torso of the user to provide support for the user's upper arm or humerus. An actuator extends between the base and the upper arm support to drive the upper arm support about the hinged connection to the base. This movement causes the abduction and adduction of the user's arm about the shoulder.

A forearm support extends from the upper arm support and pivots about an axis of rotation relative to the upper arm support. The forearm support is also linked to the base. As the actuator drives the upper arm support through an arc about the hinge connection with the base, the link between the forearm support and the base operates to pivot the forearm support about an axis of rotation relative to the upper support. The degree of rotation can be adjusted. This movement can also be eliminated. The rotational movement between the upper arm support and the forearm support causes the rotation of the arm about the shoulder. The device achieves simultaneous rotation and abduction and adduction with a single drive mechanism.

The degree of motion for both types of motion can be varied with the machine. The actuator is a bidirectional linear actuator. As the length of the stroke is varied, so is the range of abduction, and subsequent range of adduction. The range of rotation is controlled by the link between the forearm support and the base. The forearm support is mounted on a shaft which is joined by a pin in a yoke at one end of the link. The other end of the link follows a straight line which forms an angle with the direction of linear actuation. As the actuator pivots the upper arm support and the forearm support upward, the link is drawn upward. As the link follows the straight line laterally, it pivots and causes the shaft on which the forearm support is mounted to pivot. This straight line can be provided, for example, by a slot. The angle of the line relative to the direction of linear actuation can be adjusted to change the degree of rotation of the arm about the shoulder.

The forearm support includes a forearm rest mount linked to the upper arm support by a shaft. A forearm rest cooperates with the mount to provide a plane on which the forearm can be positioned. The forearm rest can be angularly positioned on the mount to change the angle of bend in the elbow and to vary the device for use with the right side and left side.

The base and the actuator are concealed within a housing to protect the user from being harmed by the mechanism of the device. The housing is preferably constructed from lightweight plastic and includes a chamber having a back wall, a bottom wall, and two side walls. The upper arm support forms the upper surface. The front cover comprises a lower member which is stationary relative to the chamber, and an upper member which is hinged to the upper arm support. As the upper arm support is pivoted about the base to raise the arm, the upper cover member slides up relative to the lower cover member and as the arm is lowered, the upper cover member slides down the lower cover member. Wings extend from the side of the upper arm support into the chamber and cooperate with the side walls. These wings conceal the sides of the housing when the upper arm support is raised, and slide back into the housing as the upper arm support is lowered.

BRIEF DESCRIPTION OF THE DRAWINGS

FIG. 1 is a front perspective view of the passive motion device in accordance with the present invention;

FIG. 2 is a front elevational view of a user with the device showing the arm in an externally rotated and abducted position;

FIG. 3 is a front elevational view of a user with the device showing the arm in an internally rotated and abducted position;

DETAILED DESCRIPTION OF THE DRAWINGS

Figure 4:
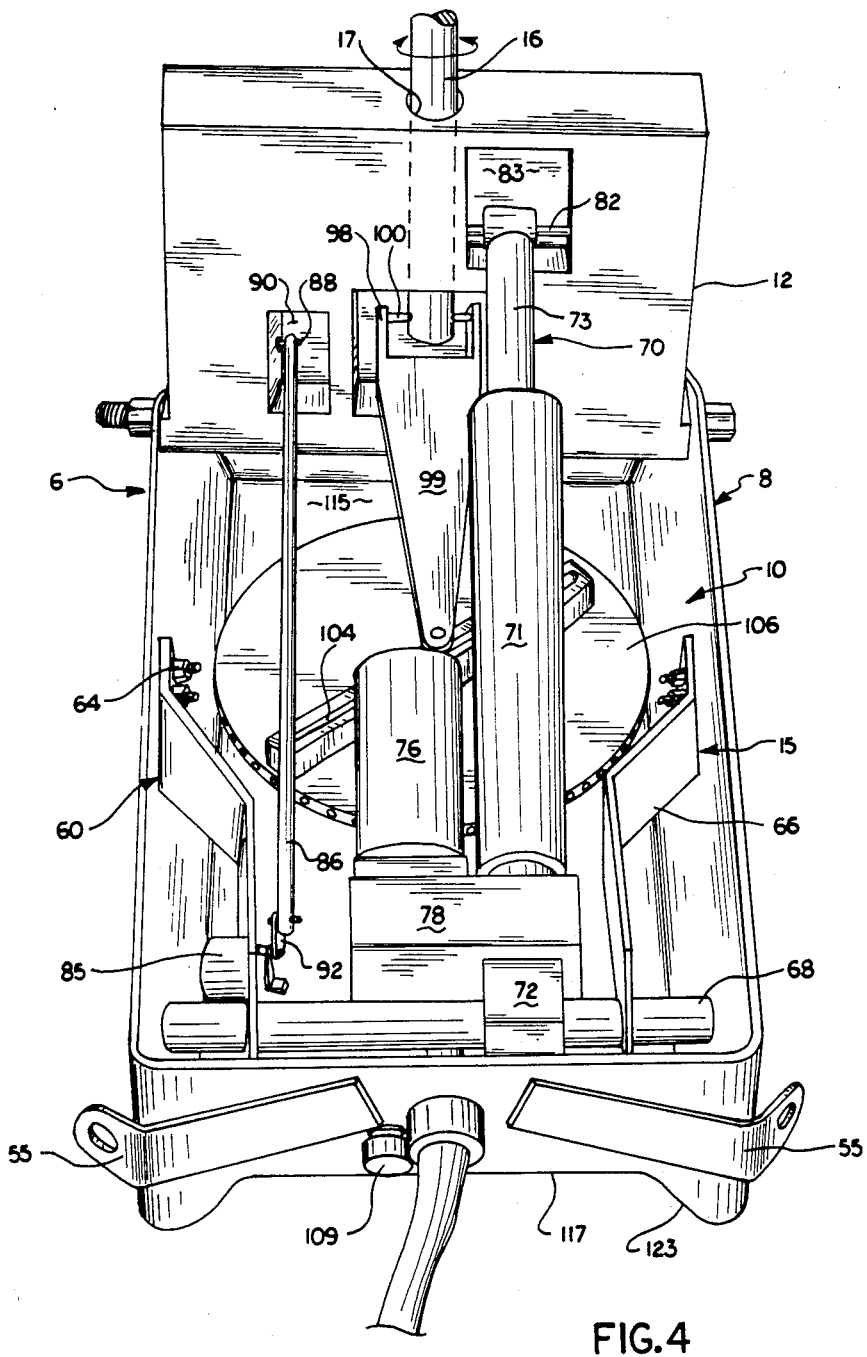
FIG. 4 is a front perspective view of the device with the front cover removed.

An actuator unit 6 and a control unit 7 of a device in accordance with the invention are shown in FIG. 1. The actuator unit 6 includes an upper arm support 12 which is pivotably connected along the top edge 5 by hinges 13 to a base 10. The base 10 includes a frame 15 and the housing 8 for the actuator unit 6. A forearm support 14 is joined to the upper arm support 12 by a shaft 16. The forearm support 14 includes a forearm rest 30 which fits on a forearm rest mount 32.

The actuator unit 6 is contained in the housing 8 which is part of the base 10. The back wall 9 of the housing 8 fits against the lateral portion of the torso of the user and extends along the user's side from the armpit or axilla along the lateral portions of the thorax and abdomen to the hip or ileac crest of the user. The top edge 5 of the actuator unit 6 formed where the upper arm support 12 cooperates with the housing 8 fits under the armpit of the user. The upper arm, or humerus, is supported by the upper arm support 12, and the forearm, including the ulna and the radius, are supported by the forearm support 14.

The forearm rest 30 is generally rectangular and of sufficient length to provide comfortable support for a child's or adult's forearm and optionally for the wrist and hand as well. The length may be, for example, from five to twenty inches. The width should also be sufficient to support a forearm which is positioned with the palm side of the hand down, e.g., from three to six inches across.

The forearm rest mount 32 is circular and is fixed to one end of the shaft 16. The forearm rest 30 fits over the mount 32. The rest 30 is held in position on the mount 32 by a central pin 34 and is locked in position on the mount 32 by a locking mechanism 33. The position of the central pin 34 corresponds approximately to the position of the elbow when the device is in use. Thus, the angle between the upper arm and the forearm corresponds to the angle between the forearm rest 30 and the shaft 16 which lies along the longitudinal axis of the upper arm support 12. The shaft 16 projects through a slot 35 in the forearm rest 30. The forearm rest 30 pivots about the central pin 34. The position of the forearm rest 30 on the forearm rest mount 32 can be varied to accommodate varying degrees of bend in the elbow. When the longitudinal axis of the forearm rest 30 is aligned with the shaft 16, the user's arm is extended. The position of the forearm rest 30 can be adjusted to provide an angle at the elbow of about 90° to about 180°.

The forearm rest mount 32 is provided with internal detents (not shown). The detents are positioned to allow the angle of the forearm rest 30 to be positioned at 15° increments. A dowel 36 (FIG. 2) mounted on the forearm rest 30 is biased by a spring (not shown) into the detents to lock the forearm rest 30 into position against the forearm mount 32.

This feature also allows the actuator unit 6 to be adjusted for use with the right or left shoulder by pivoting the forearm rest 30 to reposition it on the forearm rest mount 32. The actuator unit 6 in FIG. 1 is shown with the forearm rest 30 in position for use with a right shoulder. The position of the forearm rest 30 for use with the left shoulder is shown in phantom lines.

FIGS. 2 and 3 illustrate a person who is using the device to impart continuous passive motion to his shoulder. In FIG. 2 the arm is seen at a raised or abducted position, with the arm externally rotated. In FIG. 3, the arm has been lowered, or abducted, and rotated internally.

The actuator unit 6 rests on the top of the hip of the user and is held in position under the user's arms by a harness 49. The weight of the device, which is under fifteen pounds, and preferably ten pounds or less, is borne on the user's hip and the shoulder which is not being treated. Adjustable lower and upper horizontal straps 50, 52, having pads 40, 42, hold the actuator unit 6 against the user's rib cage. An adjustable shoulder strap 54 distributes the weight of the actuator unit 6 on the user's shoulder. The shoulder strap 54 includes a pad 56. The pad 42 for the upper horizontal strap includes loops 43 which hold the shoulder strap 54 in position away from the tendon which is on the side of the user's neck. The straps are fastened to the actuator unit 6 in a simple secure manner, such as ring snaps 57 which snap into support flanges 55. This arrangement results in a CPM device which can be worn by the user and permits mobility while the user is subjected to treatment. This facilitates treatment which may last for several hours or longer per session.

As seen in FIG. 4, the upper arm support 12 is pivotally connected to the base 10. In the preferred embodiment the base 10 includes a frame which is formed of an actuator bracket 60 which is fastened to the inside of the housing 8 and to side bars 62 (FIG. 1) which are mounted on the outside of the housing 8 and are also fastened to the actuator bracket 60 by bolts 64. Of course, if the housing is sufficiently stable, it may be unnecessary to provide an internal frame and the moving elements may be mounted directly to the housing.

Figure 8:
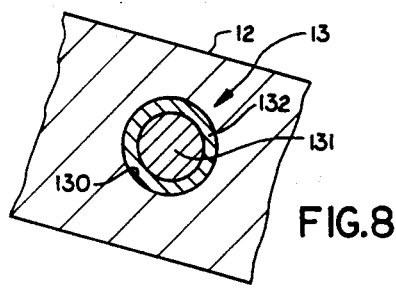
FIG. 8 is a cross section of the hinge means between the upper arm support and the base.

In FIG. 4 the covering elements of the housing 8 have been removed to show that the upper arm support 12 is pivotally connected to the base 10 of the actuator unit 6. This pivotal connection 13 (shown in detail in FIG. 8) is formed by a metal rod 131 which extends across a bore 130 in the upper arm support 12. The bolts 59 hold the rod 131 to the side bars 62. Plastic bushings 132 in the bore 13 of the upper arm support 12 form the bearing surfaces.

The frame 15 provides a basis for the drive mechanism to work against and provides stability. It includes side bars 62 (FIG. 1) and a modified U-shaped actuator bracket 60 (FIG. 4). Side bars 62 are mounted on the outside of both side walls 11 of the housing 8. The side bars 62 are joined to the actuator bracket 60 portion of the frame 15 by means of bolts 64. The actuator bracket 62 is internal to the housing 8. The bolts 64 hold the frame 15 in position in the housing 8. The actuator bracket 60 includes two cheek bars 66 which are stepped to provide additional dampening of sound. A rod 68 is mounted between the cheek bars 66.

The drive mechanism 70 is mounted to the rod 68 of the frame 15 by means of a mount ring or sleeve 72 which encircles the rod 68 and which is free to pivot about the rod 68. The drive mechanism 70 can be a linear actuator 71 having a forward and reverse stroke such as a ball screw or a pneumatic cylinder. The actuator 71 preferably is powered by a motor 76. The drive motor 76 is preferably a conventional 12-volt D.C. bidirectional motor. The power is transmitted to the actuator in a known manner such as through a transmission 78 having appropriate gears. As the drive motor 76 is operated, the drive shaft 73 of the actuator will be driven at a speed determined by the selected gear reduction ratios and motor speed. The speed and length of the stroke of the drive shaft are electronically controlled by means of a control unit 7 having the appropriate circuitry.

The drive shaft 73 is pivotally mounted on an axle 82 in a recess 83 in the upper arm support 12. As the drive shaft 73 is driven upward, the upper arm support 12 pivots about the axis defined at the bolts 59 to cause abduction of the user's arm. The angle between the longitudinal axis of the upper arm support 12 and the longitudinal axis of the base 20 defines the angle of abduction of the shoulder, and is constant when the device is at rest. As the drive shaft 73 is retracted, the upper arm support pivots at the bolts 59 to cause adduction of the user's arm. This varies the angle of abduction. As the upper arm support is moved, the shoulder is exercised. The degree of displacement of the angle of abduction from the raised to lowered portion defines the range of exercise or abduction and adduction to which the shoulder is subjected.

As the upper arm support 12 is pivoted, the motion is translated to a potentiometer 85 by a rod 86 pivotally mounted on a pin 88 in a recess 90 of the upper arm support 12. As the rod 86 is moved, it rotates a lever arm 92. The potentiometer 85 senses the relative displacement of the lever arm 92, and the displacement of the upper arm support 12. The potentiometer 85 feeds back to the control unit 7 a voltage proportional to the angular displacement of the lever arm 92 so that the motor can be reversed when the upper arm support 12 has been rotated through a predetermined range of abduction.

The angular displacement of the lever arm 92 corresponds to a known displacement of the upper arm support 12 and turns the potentiometer 85 through a known change in resistance. The angle between the upper arm support 12 and the base 70 is directly related to the degree of abduction or adduction of the shoulder. This potentiometer reading is compared to preset limits by the control unit 7 to determine the on-off cycle of the motor.

The control unit 7 contains the logic circuits, switches, and power circuits for operation of the drive unit 70. Implementation of this circuit is accomplished with conventional discrete components. A standard microprocessor may also be used in place of discrete components for carrying out the functions of the controller as specified herein.

The medical personnel determines the maximum range of abduction within which the injured shoulder should be exercised. The limits are inputted to the control circuit in a known manner and the position of the shoulder as represented by the potentiometer 85 setting is compared to the abduction limits to regulate the angular displacement of the upper arm support 21, i.e., the range of abduction, by the drive mechanism.

The control circuit is designed to operate in a manual or automatic mode, selection of the operating mode being controlled by the patient via a throw switch on the control unit. In manual mode used for intermittent passive motion the patient pushes either an adduct or abduct actuation switch and power is thus supplied to the motor 76 to cause the drive shaft 70 to either extend or retract and pivot the upper arm support 12. The control circuit monitors, via the potentiometer 85 reading, the degree of adduction and abduction, and inhibits the drive motor 76 whenever the preset limits are reached.

In an automatic mode used for continuous passive motion the control circuit continuously operates the motor to abduct and adduct the shoulder between the preset limits; the control circuit automatically reverses the drive motor 76 when a limit is reached. Thus, in the automatic mode the shoulder can be safely and continuously raised and lowered.

The forearm support 14 is coupled to the upper arm support 12 by the shaft 16 which is journaled in a bore 17 in the upper arm support 12. The angle between the plane of the forearm support 14 and the plane of the upper arm support 12 defines the angle of rotation of the shoulder which is constant when the actuator is at rest. A link 99 is coupled at one end to the shaft 16. The other end of the link 99 is operatively associated with the base 10 to optionally cause rotation of the shaft 16. The link is tied to a line such as formed by a slot 104. The angle formed between the slot 104 and the longitudinal axis of the linear actuator 70 will determine the amount of rotation of the shaft 16 which defines the range of rotation for the shoulder, as will be explained later.

Figure 5A:
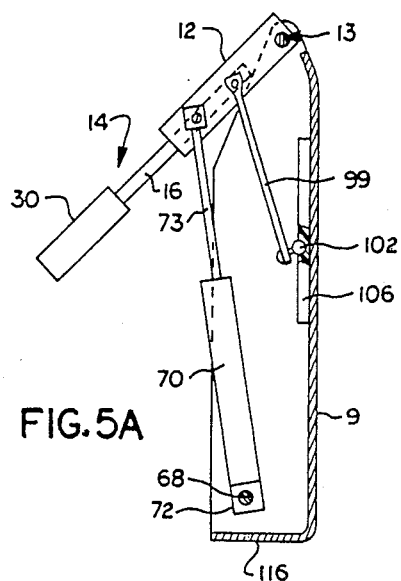
FIG. 5A is a side sectional view of the device showing the upper arm support in a lowered position and showing no rotation of the forearm support.
Figure 6A:
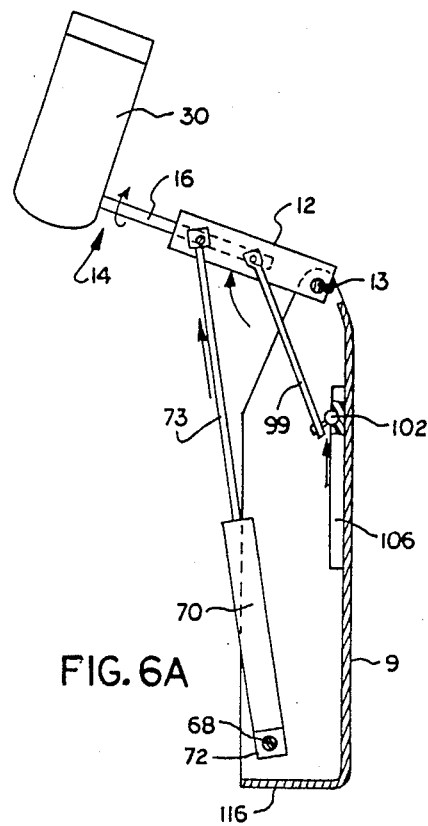
FIG. 6A is a side sectional view of the device similar to FIG. 5A, but showing the upper arm support in a raised position and showing rotation of the forearm support.

One end of the link 99 forms a yoke 98 and a pin 100 secures the shaft 16 to the legs of the yoke 98. In the preferred embodiment the link 99 is connected to a ball 102 (FIGS. 5A and 6A) which is captured in the slot 104. The ball 102 has sufficient freedom of movement in all directions to accommodate the varying relationship between the forearm rest and the base. The slot 104 is formed in a disc 106. The slot 104 is shown as a straight slot but could also be curved to vary the rate of rotation. The disc 106 is mounted to the inner face of the back wall 9 of the housing 8 to change the angle of the slot 104. It should be understood, however, that the link could also include a sleeve which is pivotally coupled to an I-rail on the disc.

Figure 5B:
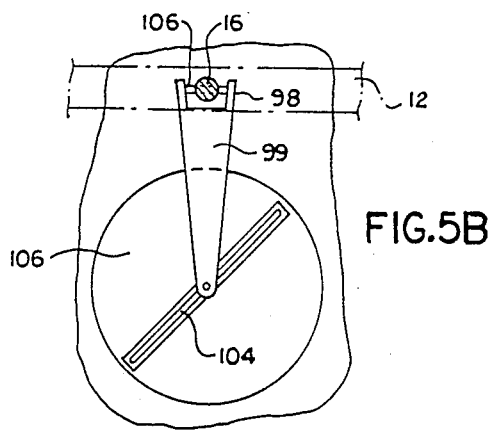
FIG. 5B is a front detail of the forearm support shaft and link of FIG. 5A.
Figure 6B:
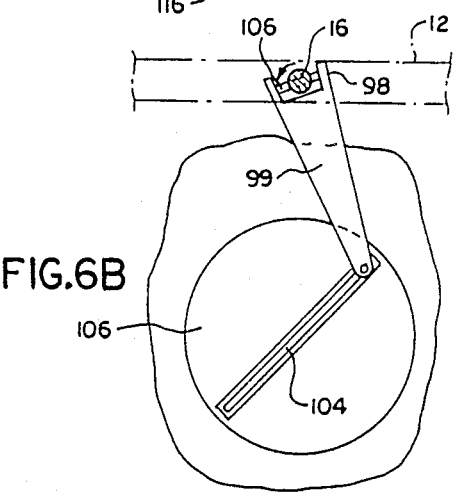
FIG. 6B is a front detail of the forearm support shaft and link of FIG. 6A.

As can be seen in FIGS. 5 and 6, coupling the shaft 16 to the slot 104 will cause the shaft 16, and subsequently the forearm support 14, to rotate as the drive mechanism 70 causes the upper arm support 12 to pivot. As the drive mechanism 70 extends and the upper arm support 12 pivots upward, the link 99 is drawn diagonally upward and sideways along the slot 104. As the captured end of the link 99 is displaced sideways, it causes the shaft 16 to be rotated. This also causes the forearm support 14 to be rotated.

The position of the disc 106 in the housing 8 can be varied so that the angle formed between the slots 104 and the longitudinal axis of the base which corresponds to the longitudinal axis of the linear actuator can be varied. This angle of the slot 104 determines the relative amount of rotational displacement of the forearm support 14 as the upper arm support 12 is pivoted by the drive mechanism 70. If the slot 104 is in a vertical position, then no rotation will occur. As the slot 104 is adjusted to a more horizontal position, a greater range of rotation will occur. The design will result in a range of about 20° of rotation in either direction for a total range of about 40° of rotation where the 0 axis is the position of the arm hanging straight.

Figure 7:
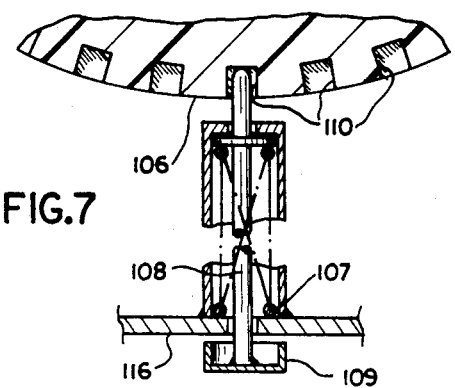
FIG. 7 is a detail of the detent for the disc forming the rotation slot.

As shown in FIG. 7, a pin 108 is biased by a spring 107 into detents 110 on the disc 106 to lock the disc 106 into place. In order to change the location of the disc 106, the pin 108 is withdrawn from the detents 110 by pulling the knob 109. The disc 106 is rotated to the desired position by manually changing the position of the forearm support 14. The forearm support 14 should be at the beginning or end of the stroke to rotate the disc 106. The pin 108 is then allowed to snap back into the proper detent.

The actuator unit 6 includes the housing 8 formed of sheet plastic or some other suitably lightweight material. The housing 8 is comprised of a chamber 115 (FIG. 4) which houses the frame 15 and the drive mechanism 70. The side bars 62 act to stabilize the housing 8 against lateral torque and allow the use of lightweight material for the housing. The chamber 115 has the back wall 9, side walls 11, and a bottom wall 116. The back wall 9 of the housing 8 flares out at either side to form a recess 117 to accommodate the hip of the user so that the device is supported on the user's hip. The top of the chamber 115 curves gently to the pivot point of the upper arm support 12 to accommodate the armpit of the user. The upper arm support 12 forms the top of the housing 8. The front of the chamber 115 is closed by a two member cover 118 (FIG. 1). The lower member 119 of the cover includes a bottom flange 120 which fits over the bottom wall 116 of the chamber 115 to hold the lower member 119 in place. The top member 121 of the cover is hinged to the upper arm support 12. The sides fold to form side flanges 123 (FIG. 4) which fit in between the side walls 11 of the housing and the lower member 119 of the cover. The top member 121 acts to conceal the inner mechanism of the actuator unit 6 as the upper arm support 12 is pivoted upward. The top member 121 slides up along the lower member 119 and outward as the arm is abducted and back down along the lower member 119, as can be seen in FIGS. 2 and 3.

Use of the device can be envisioned as follows. Initially, the device is adjusted to account for the therapy for use with the particular user. The angle between the forearm and the upper arm at the elbow is adjusted by disengaging the dowel 36 from the detents, holding the forearm rest 30 in position on the forearm rest mount 32, pivoting the forearm rest 30 about the central pin 34 to the desired position on the forearm arm rest mount 32, and re-engaging the dowel 36 in the proper detent to lock the forearm rest 30 into the proper position. The range of rotation is selected by adjustment of the angle of the rotation slot by disengaging the rod 108 from the detents 110 in the disc 106 and, while maintaining the rod in a withdrawn position, rotating the position of the disc by rotating the forearm rest 30 to the desired angle of rotation which forms the upper or lower extreme of the range of rotation, and subsequently re-engaging the rod 108 into the detent 110.

The medical personnel having determined the proper range of adduction and abduction for the arm, inputs this information into the control unit 7, which will control the range of abduction and adduction by reading the voltage from the potentiometer 85. When the predetermined extreme angles of abduction or adduction are reached, then the linear actuator 70 will be reversed.

The device is then mounted on the user. The device is placed against the lateral portion of the torso of the user, with the upper arm support 12 cooperating with the top portion of the upper arm of the user, and the backwall 9 of the housing 8 securely against the user's rib cage extending from the axilla along the lateral portions of the thorax and the abdomen to the ileac crest. The user's torso fits into the recess 117 and the side flanges 123 will rest against the user's hips (ileac crest) to help bear the weight of the device.

The horizontal straps 50 and 52 and pads 40 and 42 are adjusted on the user and snapped to the rings 55 on the device. The shoulder strap pad 54 is fed through the proper loop 43 and adjusted to distribute the weight on the shoulder and to avoid bearing on the tendons at the top of the user's shoulder. Two loops 43 are provided to account for different sized users.

It is then envisioned that the device will be activated for continuous motion of the user's shoulder, causing both abduction and adduction and rotation. The proper periods of treatment are to be determined by the medical personnel. The machine may also be used while the user is asleep. The machine may be applied immediately following the shoulder operation before the user has regained consciousness.

In order to adjust the device for use from a right-hand machine to a left-hand machine, the position of the forearm rest 30 must be changed on the forearm rest mount 32 by releasing the dowel 36 from its detent and pivoting the forearm rest 30 about the central pin 34 to the proper position on the forearm rest mount 32. The dowel 36 is then allowed to snap back into position in the proper detent.

The angle of the slot 104 must also be rotated. The slot is repositioned by disengaging the rod 108 from the detents 110 in the disc 106, repositioning the disc by manually rotating the forearm support 14 and drawing it into the proper position, and re-engaging the rod 108 in the detents 110. The forearm support 14 should be at the top or bottom of the stroke, and preferably the bottom of the stroke, before it is repositioned.

The slot is in proper position for use with the right arm when it extends at an angle from the bottom left to the top right of the disc, or when it is oriented in the first and third quadrants. Rotation is proper for use with the left hand when the slot forms an angle relative to the linear actuator which extends from the bottom right to the top left, or when the axis of the slot is in the second and fourth quadrant of a Cartesian system. When the slot is in a vertical position and there is no angle between the axis of the slot 104 and the linear actuator 70, then no rotation of the forearm rest 30 is produced, i.e., the range of rotation is 0°.

As it is important that the device is portable, both from the standpoint that it is possible that it must be carried from room to room in the hospital, and also that it is of an advantage to provide a machine which allows a certain amount of mobility for the user, the device is designed to be as light as possible. Thus, where it is possible, the parts such as the disc 106, the housing 8, the forearm rest 30 and forearm rest mount 32 are constructed of a lightweight rigid plastic. The forearm rest 30 is preferably hollow and, in addition, members such as the upper arm mount 12 and the forearm rest mount 32 may include waffling to make them lighter weight. It is preferred that the device weigh not more than 15 pounds, and preferably that it weigh 10 pounds or less.

While the invention has been shown and described with respect to a particular embodiment thereof, this is for the purpose of illustration rather than limitation, and other variations and modifications of the specific embodiment herein shown and described, all within the intended spirit and scope of the invention, will be apparent to those skilled in the art. Accordingly, the patent is not to be limited in scope and effect to the specific embodiment herein shown and described nor in any other way that is inconsistent with the extent to which the progress in the art has been advanced by the invention.

What is claimed is:

1. A portable device which can be worn by a user to impart continuous passive motion to the user's shoulder, comprising:
    a base including a housing which engages an adjacent lateral portion of the user's torso;
    an arm support pivotally joined to the base comprising an upper arm support which engages an adjacent portion of the user's upper arm, a lower arm support which engages an adjacent portion of the user's lower arm, and a shaft, the upper arm support having a longitudinal axis and extending from the base to form an angle whereby the angle of the upper arm support relative to the base defines an angle of abduction corresponding to the degree of abduction of the user's shoulder, the shaft being supported by and extending from the upper arm support along the longitudinal axis and being rotatable relative to the upper arm support about the longitudinal axis, the forearm support being pivotally mounted on the shaft to link the forearm support and the upper arm support in selectable positions and forming an angle of the forearm support relative to the base whereby the angle of the forearm support relative to the base defines an angle of rotation corresponding to the degree of rotation of the user's shoulder;
    a drive mechanism including an actuator operatively joined between the base and the arm support to cause the upper arm support to pivot relative to the base and to displace the angle of abduction and define a range of abduction when the drive mechanism is activated, the actuator being contained within the housing; and
    a rigid link having first and second ends and operatively joined at the first end to the shaft and at the second end to the base to optionally cause the shaft and the forearm support to rotate about the longitudinal axis to displace the angle of rotation and define a range of rotation when the device mechanism is activated to displace the angle of abduction.

2. A device as set forth in claim 1, wherein the base includes a member which forms a slot and the second end of the link cooperates with the slot, the position of the slot defining the range of rotation.

3. A device as set forth in claim 2, wherein the position of the member forming the slot can be adjusted to vary the range of rotation.

4. A device as set forth in claim 3, wherein the drive mechanism is a linear actuator which has a forward and reverse stroke.

5. A device as set forth in claim 4, wherein the length of the stroke can be changed to vary the range of abduction.

6. A device as set forth in claim 5, wherein a potentiometer is used to determine the range of abduction, and which will cause the actuator to change directions when either extreme of the predetermined range of abduction is reached.

7. A device as set forth in claim 6, wherein a rod is pivotally joined at one end to the upper arm support and is joined at the other end to a lever, and the relative displacement of the upper arm support is transmitted by said rod to said lever, the potentiometer sensing the relative displacement of said lever to determine the range of abduction.

8. A device as set forth in claim 1, wherein the forearm support includes a forearm rest positioned on a forearm rest mount and the angle formed between the longitudinal axis of the forearm rest and the upper arm support can be adjusted by varying the position of the forearm rest on the forearm rest mount.

9. A device as set forth in claim 8, wherein the forearm rest is pivotally mounted on the forearm rest mount and is releasably locked in position by a detent.

10. A device as set forth in claim 1, including means to adapt said device for use with a right or left shoulder.

11. A device as set forth in claim 10, wherein the forearm support comprises a shaft which rotates relative to the upper arm support, and a mount member at the end of the forearm support, said mount member supporting a forearm rest, said forearm rest positionable relative to the mount member to adjust the angle between the forearm rest and the upper arm support.

12. A device as set forth in claim 1, wherein said device includes means to impart rotation to either the right or the left shoulder.

13. A device as set forth in claim 1, wherein:
said housing includes a chamber having a back wall, two side walls, a bottom wall, and a cover; and
said upper arm support being pivotally connected to the chamber, said cover cooperating with said upper arm support to follow the motion of the upper arm support, so that the drive mechanism remains concealed within the housing during operation of the drive mechanism.

14. A device as set forth in claim 13, wherein said cover includes a top member and a bottom member and said top member is joined to the upper arm support and the top and bottom members are in sliding cooperation as the upper arm support is driven to vary the range of abduction of the shoulder.

15. A device as set forth in claim 1, wherein said housing includes a curved back wall which cooperates with the torso of a user.

16. A device as set forth in claim 15, wherein said back wall is flared at the lower end to cooperate with and be supported by a hip of the user.

17. A device as set forth in claim 1, wherein the device weighs less than about 15 lbs.

18. A device as set forth in claim 1, wherein the device is secured to the user's body by a harness.

19. A device as set forth in claim 18, wherein the harness includes a first and second horizontal strap and a shoulder strap and the shoulder strap is linked to a horizontal strap to hold the shoulder strap away from the user's neck.

* * * * *